(12) United States Patent
Wan et al.

(10) Patent No.: US 10,001,494 B2
(45) Date of Patent: Jun. 19, 2018

(54) AUTOMATIC FECAL OCCULT BLOOD DETECTOR

(71) Applicant: W.H.P.M. BIORESEARCH AND TECHNOLOGY CO., LTD., Beijing (CN)

(72) Inventors: John Wan, Beijing (CN); Yunfei Zhang, Beijing (CN); Jie Liu, Beijing (CN); Qinghai Xia, Beijing (CN)

(73) Assignee: W.H.P.M. BIORESEARCH AND TECHNOLOGY CO., LTD, Beijing (CN)

( * ) Notice: Subject to any disclaimer, the term of this patent is extended or adjusted under 35 U.S.C. 154(b) by 93 days.

(21) Appl. No.: 15/031,367

(22) PCT Filed: Oct. 24, 2014

(86) PCT No.: PCT/CN2014/089386
§ 371 (c)(1),
(2) Date: Apr. 22, 2016

(87) PCT Pub. No.: WO2015/058706
PCT Pub. Date: Apr. 30, 2015

(65) Prior Publication Data
US 2016/0266150 A1    Sep. 15, 2016

(30) Foreign Application Priority Data
Oct. 25, 2013    (CN) .......................... 2013 1 0514057

(51) Int. Cl.
*G01N 33/48*    (2006.01)
*G01N 33/72*    (2006.01)
(Continued)

(52) U.S. Cl.
CPC .......... *G01N 33/72* (2013.01); *A61B 10/0038* (2013.01); *B01L 3/5029* (2013.01);
(Continued)

(58) Field of Classification Search
CPC ........ G01N 21/13; G01N 33/48; G01N 35/02; G01N 35/04; B01L 2200/18
See application file for complete search history.

(56) References Cited

U.S. PATENT DOCUMENTS 7,771,659 B2 *    8/2010    Ziegler .................. G01N 15/05
                                                                356/246
8,262,994 B2 *    9/2012    Hamada ............... G01N 35/026
                                                                422/63
(Continued)

FOREIGN PATENT DOCUMENTS

CN    1932514 A    3/2007
CN    201926666 U    8/2011
(Continued)

OTHER PUBLICATIONS

Machine translation of JP H06-174729, downloaded Sep. 20, 2017.*
Supplementary European Search Report issued in Application No. EP 14 85 5965 dated Jun. 22, 2017.

*Primary Examiner* — Jan Ludlow
(74) *Attorney, Agent, or Firm* — Scully Scott Murphy & Presser

(57) ABSTRACT

The present invention discloses an automatic fecal occult blood detector for detecting a sample kit, comprising: a feed passage and a discharging passage which are provided in parallel and convey a sample kit separately; a transfer platform configured between the feed passage and the discharging passage; a push rod configured to push the sample kit on the feed passage onto the discharging passage through the transfer platform; and an image capturing device provided on one side of the discharging passage to acquire the color band information presented on a test strip. In the present invention, the parallel arrangement of the feed passage and the discharging passage shortens the whole length of the automatic detector, meeting the requirement (Continued)

that the color band information of the test strip is automatically acquired after the sample kit is left in the device a certain time.

10 Claims, 6 Drawing Sheets

(51) Int. Cl.
  *A61B 10/00* (2006.01)
  *G01N 35/04* (2006.01)
  *B01L 3/00* (2006.01)
  *G01N 35/02* (2006.01)
  *G01N 35/00* (2006.01)

(52) U.S. Cl.
  CPC ..... *G01N 35/00029* (2013.01); *G01N 35/021* (2013.01); *G01N 35/04* (2013.01); *B01L 2300/046* (2013.01); *B01L 2400/0683* (2013.01); *G01N 2035/00089* (2013.01); *G01N 2035/00128* (2013.01); *G01N 2035/0406* (2013.01); *G01N 2035/0429* (2013.01); *G01N 2035/0484* (2013.01)

(56) References Cited

U.S. PATENT DOCUMENTS

2011/0189053 A1* 8/2011 Tatsutani ............... G01N 33/48 422/68.1
2013/0222634 A1 8/2013 Setlur et al.

FOREIGN PATENT DOCUMENTS

CN 102252968 A 11/2011
JP 6-174729 A 6/1994

* cited by examiner

AUTOMATIC FECAL OCCULT BLOOD DETECTOR

TECHNICAL FIELD OF THE INVENTION

The present invention relates to an automatic fecal occult blood detector.

BACKGROUND OF THE INVENTION

Fecal occult blood refers to minor gastrointestinal bleeding. For erythrocytes are digested and damaged, the minor gastrointestinal bleeding causes no change in the color of excrement and no abnormal change in the appearance of excrement and therefore cannot be verified visually or microscopically unless the existence of few erythrocytes in excrement is found through an excrement test. The prolonged minor bleeding, the minor gastrointestinal bleeding is usually accompanied by symptoms of anemia.

As fecal occult blood cannot be directly found visually, the early malignant tumor of digestive tract in the majority of patients cannot be found timely to be intervened and treated in the early stage, which delays the optimal treatment time. Fecal occult blood can be currently detected with two test strips, one for detecting the content of hemoglobin in an excrement sample, and the other for detecting the content of transferrin. Certainly, hemoglobin and transferrin may be synchronously detected with one test strip, and the detection result can be identified by reading the color band information on the test strip, referring to the patent document CN200953022Y of the inventor for detail.

A sample kit for detecting fecal occult blood with a test strip is disclosed in the Chinese patent with application No. 201310097892.7, which comprises: a transparent sleeve 3 and an excrement collector and a plug 4 which are placed inside the sleeve 3, wherein the plug 4 is provided with a test strip 5, the excrement collector 1 comprises a main tube 1c, a handle 1a and a sampling rod 1b extending downwards from the lower end of the handle 1a, and a separating plate is provided inside the main tube 1c to divide the main tube 1c into an upper chamber and a lower chamber in which diluent is loaded. The lower end of the main tube 1c is sealed with an easily-torn material.

After collecting an excrement sample, the patient inserts the sampling rod 1b into the main tube 1c, tightly screws or presses the handle 1a, places the excrement collector in the transparent sleeve 3, and presses the excrement collector, then, the easily-torn material on the lower end of the main tube 1c is punctured, the diluent carrying the excrement sample flows out, contacts the bottom of the test strip 5 on the plug 4 and then creeps the test strip 5, thereby realizing a detection function.

The color band of the test strip generates a color after the test strip 5 is crept and placed for a given time, the color band information presented on the test strip is manually read to determine a detection result. Due to the time span of color generation, in the case where a great many of sample kits are processed, the workload of manual reading is heavy while the efficiency is low and errors occur frequently, thus, it is urgent to provide an automatic fecal occult blood detector.

SUMMARY OF THE INVENTION

The present invention aims to provide an automatic fecal occult blood detector to realize the automatic acquisition of the detection result of an excrement collecting and detecting device.

In view of this, the present invention discloses an automatic fecal occult blood detector for detecting a sample kit comprising a transparent sleeve and an excrement collector and a test strip placed in the transparent sleeve. The automatic fecal occult blood detector comprises: a feed passage and a discharging passage which are provided in parallel and convey a sample kit separately; a transfer platform configured between the feed passage and the discharging passage; a push rod configured to push the sample kit on the feed passage onto the discharging passage through the transfer platform; and an image capturing device provided on one side of the discharging passage to acquire the color band information presented on the test strip.

Further, a guide slot is provided on the transfer platform to guide the movement of the sample kit to prevent the moving sample kit from falling leftwards or rightwards.

Further, a positioning frame is provided on the push rod to accommodate the sample kit from the feed passage to prevent the moving sample kit from falling forward or backward.

Further, the automatic fecal occult blood detector comprises a pressing member which is fixed on the transfer platform to press the excrement collector during the movement process of the sample kit.

Further, the pressing member is a pressure plate which comprises a lateral plate part fixed on the transfer platform and a plate hook part extending down from the top of the lateral plate part in a curved form, wherein the lower edge of the plate hook part forms a slope surface propped against the excrement collector.

Further, the pressing member is a rolling pressure member.

Further, the automatic fecal occult blood detector comprises a push plate mechanism which is provided on the discharging passage to push the sample kit out of the discharging passage and located at the downstream side of the image acquiring device along the conveyance direction of the discharging passage.

Further, the automatic fecal occult blood detector comprises a code scanner configured to acquire information of an identification tag adhered on the side of the transparent sleeve opposite to the test strip.

Further, the automatic fecal occult blood detector comprises a processing unit in signal connection with the code scanner and the image capturing device to process the image information captured by the image capturing device and the information read by the code scanner to generate a detection result.

Further, the automatic fecal occult blood detector comprises a gate provided on the feed passage to stop the sample kit.

Further, a baffle and a position limiting plate spaced from the baffle in parallel are provided on the transfer platform, and a position limiting passage for holding the sample kit is formed between the baffle and the position limiting plate to prevent the moving sample kit from falling leftwards or rightwards.

Further, the automatic fecal occult blood detector comprises a top plate aligned to the top of the sample kit, wherein part of the top plate extends above the transfer platform while the other part of the top plate extends above the discharging passage to prevent the moving sample kit from falling forward or backward.

Further, the pressing member is a bearing.

In the present invention, the parallel arrangement of the feed passage and the discharging passage, on one hand, shortens the whole length of the automatic detector and, on the other hand, enables a plurality of sample kits to be detected at one time. Besides, the transfer platform is combined with the push rod, meeting the requirement that information of the identification tag adhered on the sample kit and the color band information of the test strip are automatically acquired after the sample kit is left in the device a certain time.

Apart from the foregoing purposes, features and advantages, other purposes, features and advantages of the present invention are described below in detail with reference to accompanying drawings.

BRIEF DESCRIPTION OF THE DRAWINGS

The accompanying drawings, which are included to provide a further understanding of the present invention and are incorporated in and constitute a part of this specification, illustrate embodiments of the present invention and serve to explain the principles of the present invention together with the description. In the accompanying drawings.

REFERENCE NUMERALS

| | |
|---|---|
| 1: excrement collector | 3: transparent sleeve |
| 4: plug | 5: test strip |
| 1a: handle | 1b: sampling rod |
| 1c: main tube | 11: feed passage |
| 12: push rod | 13: transfer platform |
| 14: top plate | 14a: slot |
| 15: discharging passage mechanism | 111 first belt conveyance |
| 112: first clamping wall mechanism | 151 second belt conveyance |
| 152: second claming wall | |
| 16: code scanner | 17: push plate mechanism |
| 18: gate | 18': brake |
| 19: image capturing device | 231: guide part |
| 21: drive motor | 22: bracket |
| 23: baffle | 24: position limiting plate |
| 26: motor | 27: lead screw |
| 28: sliding block | 30: sample kit |
| 31: press rod | 32: pressure plate |
| 33: rolling pressure member | 34: dynamic press block |
| 111: first belt conveyance mechanism | 112: first clamping wall |
| 151: second belt conveyance mechanism | 152: second clamping wall |
| 13a: guide slot | 12a: positioning frame |
| 321: lateral plate part | 322: plate hook part |
| 15a: start segment | 15b: guide plate |
| 171: first push plate | 172: second push plate |

DETAILED DESCRIPTION OF THE INVENTION

Embodiments of the present invention are described below in detail in conjunction with accompanying drawings, however, the present invention can be implemented in a number of different ways limited and covered by appended claims.

The automatic fecal occult blood detector of the present invention is used to detect a sample kit 30 which comprises a transparent sleeve 3 and an excrement collector 1 and a test strip 5 placed in the transparent sleeve 3, wherein an identification tag (not shown) is adhered on the side of the transparent sleeve 3 opposite to the test strip 5 to record sample information related to a patient.

Figure 1:
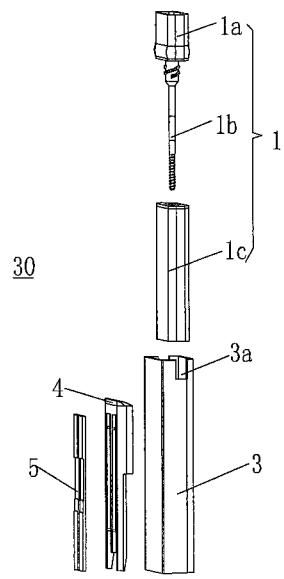
FIG. 1 is a schematic diagram illustrating the structure of an existing excrement collecting and detecting device.
Figure 2:
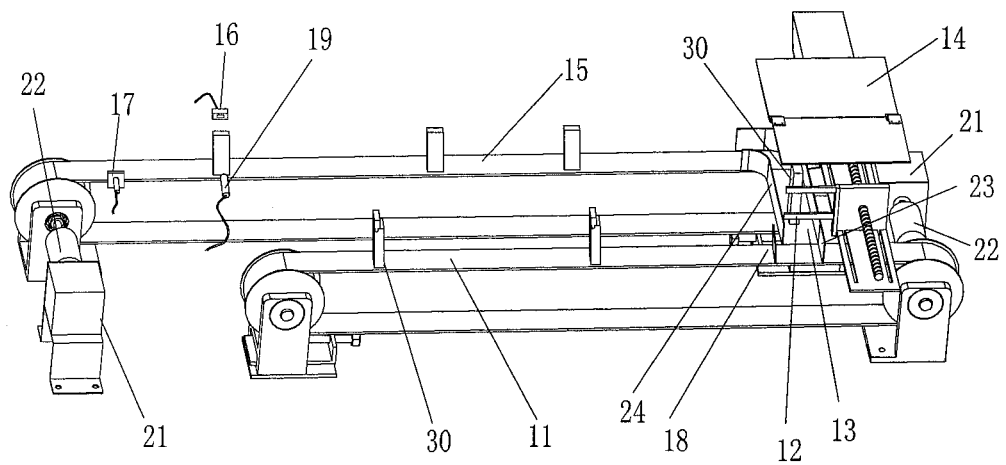
FIG. 2 is a schematic diagram illustrating the structure of an automatic fecal occult blood detector according to a first embodiment of the present invention.

FIG. 2 is a schematic diagram illustrating the structure of the automatic fecal occult blood detector of the present invention. As shown in FIG. 2, the automatic fecal occult blood detector comprises a feed passage 11 and a discharging passage 15 which are provided in parallel to convey a sample kit 30 separately; a transfer platform 13 transversely configured between the feed passage 11 and the discharging passage 15; a push rod 12 configured to push the sample kit 30 on the feed passage 11 onto the discharging passage 15 through the transfer platform 30; and a code scanner 16 and an image capturing device 19 which are symmetrically provided on two sides of the discharging passage 15, wherein the code scanner 16 acquires information of an identification tag adhered on the transparent sleeve 3, and the image capturing device 19 acquires the color band information presented on the test strip 5.

In the present invention, the image capturing device 19 may be a camera or a scanner. The identification tag is a barcode. The feed passage 11 comprises a conveyance belt, a drive motor 21 and a bracket 22 for supporting the motor, wherein the push rod 12 is fixed on a sliding block 28 which forms a lead screw-nut pair with a lead screw 27 driven by a gear motor 26.

In the present invention, the parallel arrangement of the feed passage 11 and the discharging passage 15 shortens the whole length of the automatic detector and enables a plurality of sample kits 30 to be detected at one time. Besides, the transfer platform 13 is combined with the push rod 12, meeting the requirement that information of the identification tag adhered on the sample kit 30 and the color band information of the test strip are automatically acquired after the sample kit 30 is left in the device a certain time, for example, after the test strip 5 is crept for 5 m.

Preferably, the automatic fecal occult blood detector further comprises a baffle 23 for stopping the sample kit 30 on the feed passage 11, wherein the baffle 23 runs through the transfer platform 13 and extends onto the discharging passage 15. During the running process of the feed passage 11, the baffle 23 limits the position of the sample kit 30 by stopping the sample kit 30 in front of the baffle 23.

More preferably, the baffle 23 comprises a guide part 231 for steering the sample kit 30 moving from the transfer platform 13 to the discharging passage 15. The guide part 231 extends in the conveyance direction of the discharging passage 15 after rounding from the length direction of the transfer platform 13. In a preferred embodiment of the present invention, the sample kit 30 is translated on the feed passage 11 along a first conveyance direction, on the transfer platform 13 along a second direction vertical to the first conveyance direction and on the discharging passage 15 along a third direction reverse to the first conveyance direction while being steered by 90 degrees under the combined effect of the discharging passage 15, the push rod 12 and the guide part 231 so that the side of the sample kit 30 adhered with the identification tag faces the code scanner 16.

Figure 3:
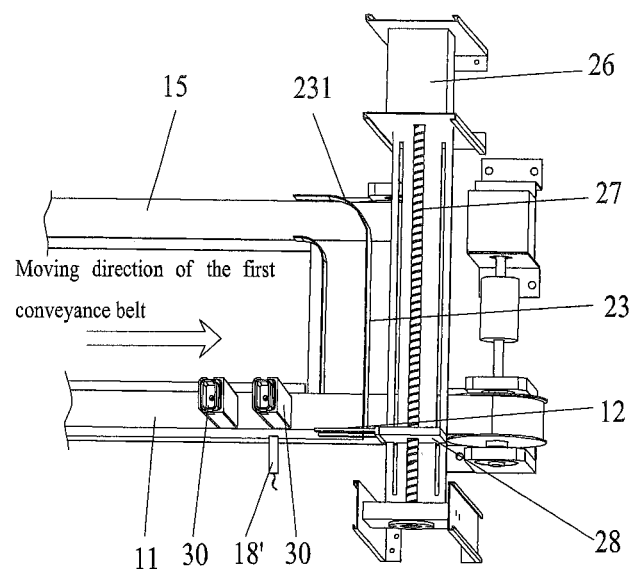
FIG. 3 is a schematic diagram illustrating the conveyance of a sample kit by the automatic fecal occult blood detector of the present invention, in which the sample kit is on a feed passage.
Figure 4:
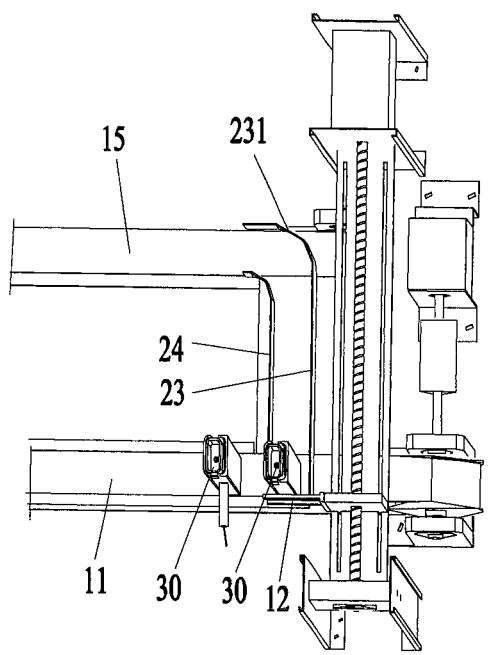
FIG. 4 is a schematic diagram illustrating the conveyance of a sample kit by the automatic fecal occult blood detector of the present invention, in which the sample kit is at a stop position on the feed passage.
Figure 5:
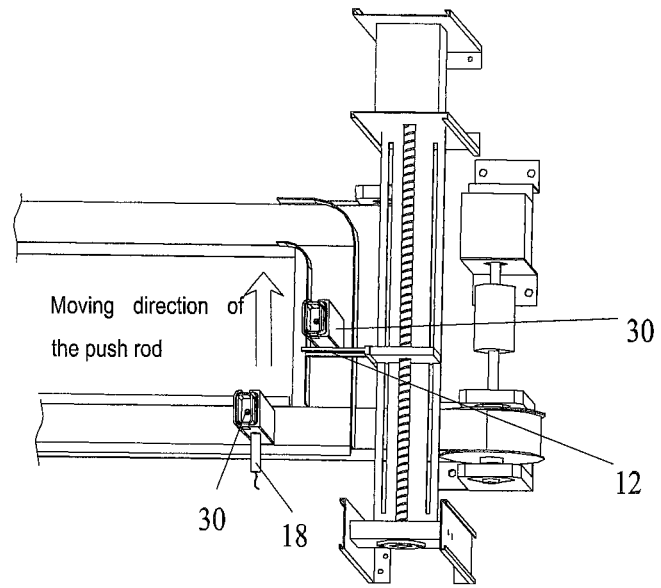
FIG. 5 is a schematic diagram illustrating the conveyance of a sample kit by the automatic fecal occult blood detector of the present invention, in which the sample kit is pushed onto a transfer platform.
Figure 6:
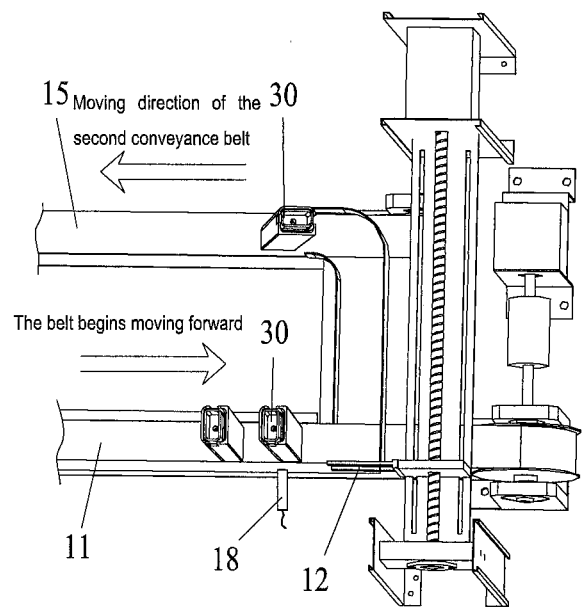
FIG. 6 is a schematic diagram illustrating the conveyance of a sample kit by the automatic fecal occult blood detector of the present invention, in which the sample kit is pushed onto a discharging passage.

Preferably, a gate 18 is provided on the feed passage 11, and as shown in FIG. 2, the gate 18 stops a sample kit 30 in front of the sample kit 30 stopped by the baffle 23. Alternatively and preferably, a brake 18' is provided on the feed passage 11, as shown in FIG. 3, to brake the sample kit 30 in front of the sample kit 30 stopped by the baffle 23 so that the sample kit 30 is laterally propped against by the brake 18' to be braked and slide with respect to the conveyance belt of the feed passage 11.

Preferably, the automatic fecal occult blood detector further comprises a processing unit (not shown) in signal connection with the code scanner 16 and the image capturing device 19 to process the image information captured by the image capturing device 19 and the information read by the code scanner 16 to generate a detection result.

Preferably, a push plate mechanism 17 is also provided on the discharging passage 15 to push an abnormal sample kit 20 out of the discharging passage 15 and the push plate mechanism 17 is located at the downstream side of the code scanner 16 and the image capturing device 19 along the conveyance direction of the discharging passage 15. Moreover, a recycling device (not shown) is provided at the rear transmission end of the discharging passage 15 to recycle a detected sample kit 30. A simplest example of the recycling device is a recycle bin.

In the present invention, a sample kit 30 is used in two kinds of modes: mode 1: the excrement collector 1 is pressed when a sample kit 30 is placed on the discharging passage 15, without passing through the transfer platform 13 and the feed passage 11; mode 2: the excrement collector 1 of the sample kit 30 is pressed on the transfer platform 13, in this case, it is needed to arrange a pressing member, such as a press rod 31, a dynamic press block 34, a pressure plate 32 or a rolling piece 33, on the transfer platform to press the excrement collector 1, and it is needed to be noted that the automatic detector used in mode 2 is also applicable to mode 1 to detect a sample kit 30.

The automatic detector needed in the second use mode of a sample kit 30 is described below in detail.

Preferably, as shown in FIG. 2, a position limiting plate 24 spaced from the baffle 23 in parallel are provided on the transfer platform 13, and a position limiting passage for holding the sample kit 30 is formed between the baffle 23 and the position limiting plate 24 to prevent the moving sample kit 30 from falling leftwards or rightwards. In this case, the width of the position limiting passage formed between the baffle 23 and the position limiting plate 24 is almost equal to the thickness of the sample kit 30. Preferably, the width of the position limiting passage can be adjusted according to the thickness of the sample kit 30. It is needed to be noted that in FIG. 2-FIG. 5, the width of the position liming passage being greater than the thickness of a sample kit 30 is applicable to the case where the excrement collector 1 is pressed before the sample kit 30 is used, and the sample kit 30 can be prevented from falling leftwards or rightwards by reducing the width of the position limiting passage to the thickness of the sample kit 30.

Preferably, the automatic fecal occult blood detector comprises a top plate 14 aligned to the top of the sample kit 30, wherein part of the top plate 14 extends above the transfer platform 13 while the other part of the top plate extends above the discharging passage 15 to prevent the pushed sample kit 30 from falling forward or backward. Apparently, the top plate 14 may extend to the feed passage 11 from the transfer platform 13 to prevent the pushed sample kit 30 from falling forward or backward.

The use of the position limiting passage in combination with the top plate 14 prevents a sample kit 30 from falling leftwards, rightwards, forwards and backwards, thus achieving the positioning of the sample kit 30.

Figure 7:
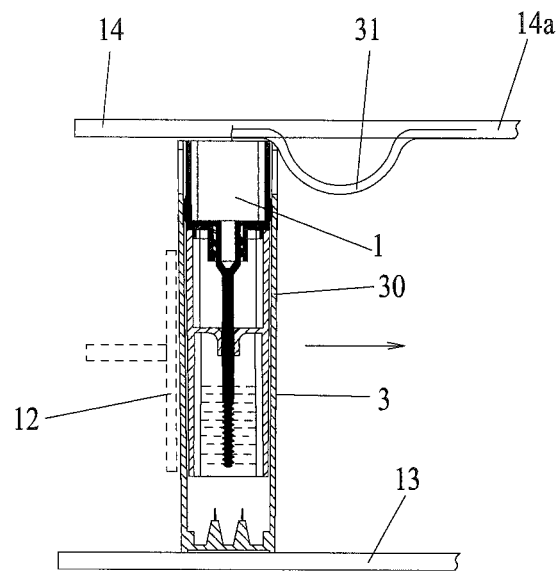
FIG. 7 is a schematic diagram illustrating the pass of a sample kit through the press rod of the automatic fecal occult blood detector of the present invention, in which a handle is not pressed.
Figure 8:
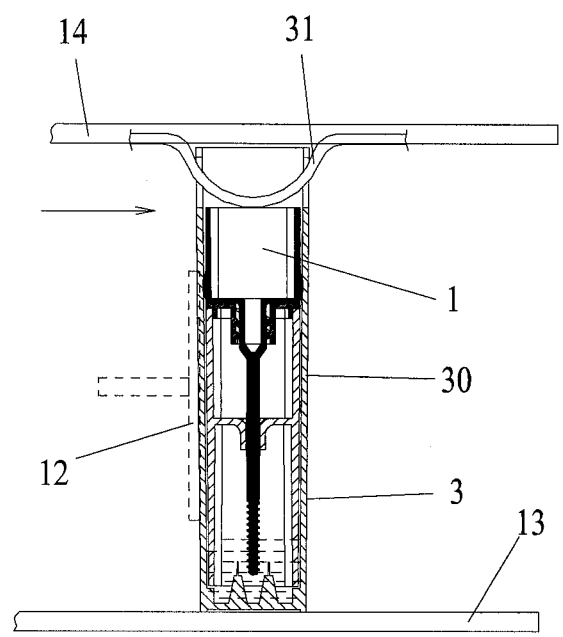
FIG. 8 is a schematic diagram illustrating the pass of a sample kit through the press rod of the automatic fecal occult blood detector of the present invention, in which a handle is pressed.

FIG. 7 and FIG. 8 are schematic diagrams illustrating the pass of a sample kit 30 from the press rod of the automatic fecal occult blood detector of the present invention. The excrement collector 1 shown in FIG. 7 is not pressed, and the excrement collector 1 shown in FIG. 8 is pressed. The pressing member is a press rod 31, a slot 14a is provided at a position on the top plate 14 corresponding to the position where the handle of the sample kit in the position limiting passage passes so that the fixed press rod 31 can be inserted into the slot 14a to be contacted with and pressed down by the top of the excrement collector 1 as the sample kit 30 is moved with the push rod 12. The press rod 31 is formed into a slope or arc shape so as to press the handle smoothly.

Figure 9:
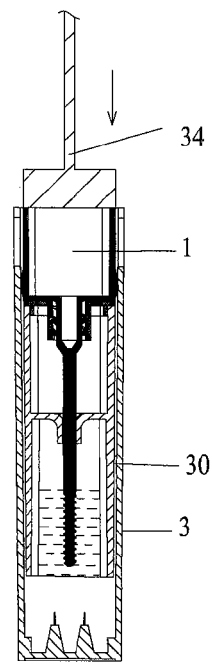
FIG. 9 is a schematic diagram illustrating the press of the pressure plate of the automatic fecal occult blood detector of the present invention on a sample kit.

FIG. 9 is a schematic diagram illustrating the pass of the pressure plate of the automatic fecal occult blood detector of the present invention on a sample kit, and different from in FIG. 7 and FIG. 8, the pressing member shown in FIG. 9 is a dynamic press block 34 which is driven by a power source to press the handle of a sample kit 30. The movement position of the push rod 12 may be correlated with the press action of the dynamic press block 34 so that the push rod 12, when moved to a specified position, is pressed by the dynamic press block 34.

It is needed to be noted that the use of the position limiting passage in combination with the top plate 14 and the press rod 31 facilitates the press on the sample kit 30, without using any additional power source.

The conveyance process of a sample kit 30 in the second use mode is described below with reference to FIG. 3 to FIG. 7.

When the detector is used, the excrement collector 1 needs to be placed in the transparent sleeve 3 with the side adhered with a patient information barcode facing outside. Then, the sample kit 30 is placed on the feed passage 11, and a control unit controls the feed passage 11 to advance with the sample kit 30 placed thereon. A plurality of sample kits 30 may be placed on the feed passage 11 at the same time, the control unit closes the gate 18 at the rear end of the feed passage 11 and stops or decelerates the feed passage 11 if the number of the sample kits 30 held on the feed passage 11 is saturated or there is a sample kit 30 on the transfer platform 13, and the gate 18 is opened and the feed passage 11 runs when the sample kit on the transfer platform 13 is successfully transferred to the discharging passage 15, thereby guaranteeing the conveyance of merely one to-be-detected sample kit 30 onto the transfer platform 13 at a time.

When the sample kit 30 is moved to the rear end of the feed passage 11, the push rod 12 pushes the sample kit 30 to the transfer platform 13, above which a press rod 31 having a certain radian or gradient is provided; when the push rod 12 pushes the sample kit 30 to move on the transfer platform 13, the press rod 31 presses the excrement collector 1 until the upper end surface of the handle of the excrement collector 1 is aligned to the notches 3a on two sides of the sleeve, at this time, the easily-torn material at the bottom of the excrement collector 1 is punctured by the thorn provided on the bottom of the sleeve, then diluent flows out carrying excrement sample, contacts the bottom of the test strip in the plug and creeps the test strip 5, thereby achieving a detection function.

When the sample kit 30 moved to the rear end of the transfer platform 13, the push rod 12 pushes the sample kit 30 to the discharging passage 15. The guide part 231 of the baffle 23 acts with the moving discharging passage 15 to change the direction of the sample kit 30 by 90 degrees so that the image capturing device 19 and the code scanner 16 provided at two sides of the conveyance belt can acquire information from the sample kit 30 moved to a proper position on the discharging passage 15.

After entering the discharging passage 15, the sample kit 30 is advanced with the discharging passage 15. The image capturing 19 device on the discharging passage 15 takes an image of the C/T line condition of the test strip in the sample kit 30 and the code scanner 16 reads the barcode information on the excrement collector 1. The control unit controls the movement speed of the discharging passage 15 so that total 5 minutes elapses from the moment the easily-torn material at the bottom of the excrement collector is punctured to the moment information is collected. After the information collection, the processing unit analyzes the display result of the C/T line and if the result is normal, a detection result is automatically generated, which may be an automatic detection report or merely contains the image of the C/T line and the barcode information for the doctor to make an analysis and then to inform the patient of a detection result. After the image is taken and the information is scanned, if the result of the C/T line is normal, then the sample kit 30 continues to be moved along with the discharging passage 15 to enter or be pushed into a recycling unit, and if the result of the C/T line is abnormal, for example, no C line is displayed or the phenomenon of strip flushing occurs, then the control unit controls the push plate of the push plate mechanism 17 to push a corresponding sample kit 30 out of the discharging passage 15, and then the patient samples new excrement to be detected.

Figure 10:
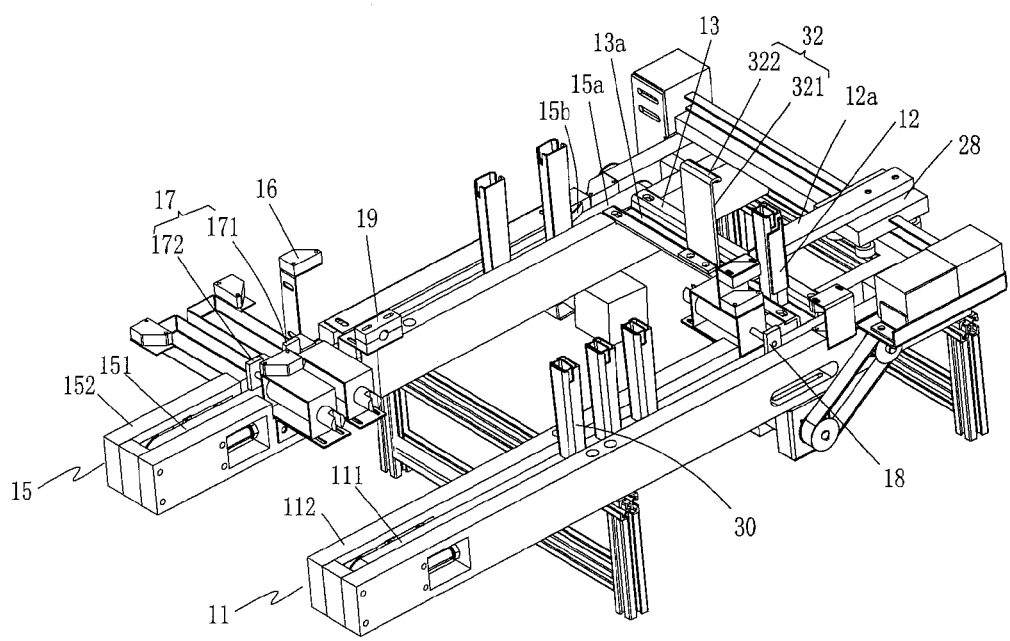
FIG. 10 is a schematic diagram illustrating the structure of an automatic fecal occult blood detector according to a second embodiment of the present invention.

FIG. 10 is a schematic diagram illustrating the structure of an automatic fecal occult blood detector according to a second embodiment of the present invention. As shown in FIG. 10, the second embodiment is different from the first embodiment in that the feed passage 11 comprises a first belt conveyance mechanism 111 and a first clamping wall 112 for the placement of a sample kit 30, the discharging passage 15 comprises a second belt conveyance mechanism 151 and a second clamping wall 152 for the placement of the sample kit 30, and the transfer platform 13 forms a guide slot 13a to guide the movement of the sample kit 30 to prevent the moving sample kit 30 from falling leftwards and rightwards.

The push rod 12 is fixed on the sliding block 28 which is driven by a belt conveyance mechanism or a chain drive, and the positioning frame 12a is provided on the push rod 12 to accommodate the sample kit 30 from the feed passage 11 to prevent the moving sample kit 30 from falling forward or backward. The cross section of the positioning frame 12a takes a U shape. With the opened side facing the feed passage 11, the opened side of the positioning frame 12a accommodates a sample kit 30 fed from the feeding passage 11; when the positioning frame 12a is translated outside the discharging passage 15, the opened side of the positioning frame 12a faces the discharging passage 15.

The pressing member is a pressure plate 32 which comprises a lateral plate part 321 fixed on the transfer platform 13 and a plate hook part 322 extending down from the top of the lateral plate part 321 in a curved form, wherein the lower edge of the plate hook part 322 is formed into a propping slope so as to press the excrement collector 1 in the transparent sleeve during the movement process of the sample kit 30.

The clamping wall of a start segment 15a of the discharging passage 15 is relatively wide so as to accommodate the transparent sleeve 3, and a guide plate 15b is provided on one side of the clamping wall so as to narrow the clamping wall until the width of the clamping wall is substantially equal to the thickness of the transparent sleeve 3 to steer the transparent sleeve 3.

The push plate mechanism 17 of the discharging passage 15 is provided with two abreast arranged push plates 171 and 172, wherein the first push plate 171 pushes an abnormal sample kit 30 into a first recycling box, and the second push plate 172 pushes a normal sample kit 30 into a second recycling box.

Besides, a detecting device, such as a code scanner, may be provided at the starting position of the feed passage 11 to detect whether or not a sample kit 30 is correctly placed by an operator and inform the operator of the reverse placement of a sample kit if the sample kit is placed reversely.

Figure 11:
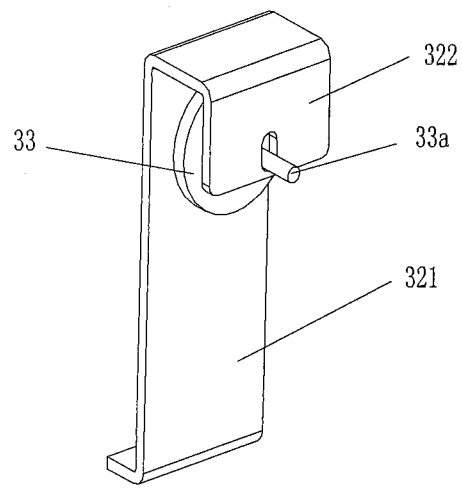
FIG. 11 is a schematic diagram illustrating the structure of a pressing member which is a press roller according to the automatic fecal occult blood detector of the present invention.
Figure 12:
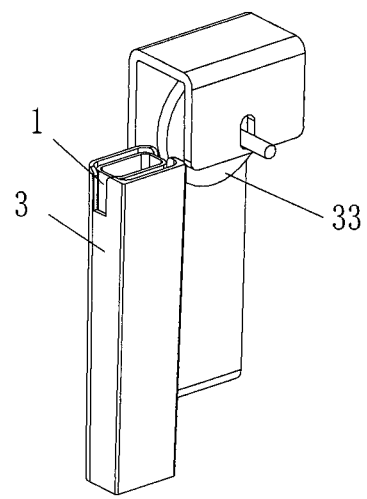
FIG. 12 is a schematic diagram illustrating the press of the pressing member which is a press roller, of the automatic fecal occult blood detector of the present invention on a sample kit.

FIG. 11 and FIG. 12 are schematic diagrams illustrating the structure of the pressing member which is a press roller according to the fecal occult blood detector disclosed herein. As shown in FIG. 11 and FIG. 12, the pressing member is a rolling pressure member 33. When a sample kit 30 passes the position of the press roller, the rolling pressure member 13 rotates while pressing the excrement collector 1 of the sample kit 30 so as to apply a smaller force to the excrement collector 1 to effectively prevent the sample kit 30 from falling down. Preferably, the rolling pressure member 33 is a bearing supported on the lateral plate part 321 and the plate hook part 322 of the pressure plate 32 by a support shaft 33a so as to be structurally compact.

According to the present invention, a fecal occult blood detector and a sample kit 30 constitute a fecal occult blood detection system in which, excrement, after sampled from a patient, is sealed in the main tube of the excrement collector. A ring of protrusions are provided on the handle of the excrement collector which are tightly jointed with the plug 4 and the internal wall of the sleeve when the excrement collector 1 is pressed to conduct a detection, thereby preventing the diluent in the sleeve carrying excrement sample from flowing outside to pollute ambient environment. The device is simple and needn't be cleaned or turned over during the detection process of the sample kit 30, which presents cross infection. The device automatically detects the sample kit 30 placed in the feed passage 11 and generates a detection result, thus, the detection efficiency is greatly improved, and the doctor is freed from the conventional detection method, improving the sense comfort level of the doctor.

It should be noted that the features of the foregoing embodiments which achieve the same function can be replaced with each other and features of different embodiments may be combined as long as no conflict is caused.

The mentioned above is merely preferred embodiments of the present invention but is not to be construed as limiting the present invention, and various variations and modifications can be made by those skilled in the art. All the modifications, equivalents and improvements devised without departing from the spirit and scope of the present invention fall within the protection scope of the present invention.

The invention claimed is:

1. A combination of a sample kit and an automatic fecal occult blood detector for detecting the sample kit,
   wherein the sample kit comprises:
      a transparent sleeve;
      an excrement collector; and
      a test strip placed in the transparent sleeve, and
   wherein the automatic fecal occult blood detector comprises:
      a feed passage and a discharging passage which are provided in parallel and convey the sample kit separately;
      a transfer platform provided between the feed passage and the discharging passage;
      a push rod configured to push the sample kit on the feed passage onto the discharging passage through the transfer platform; and
      an image capturing device provided on one side of the discharging passage to acquire color band information presented on the test strip.

2. The combination according to claim 1, wherein a guide slot is provided on the transfer platform to guide the movement of the sample kit to prevent the moving sample kit from falling leftwards or rightwards.

3. The combination according to claim 1, wherein a positioning frame is provided on the push rod to accommodate the sample kit from the feed passage to prevent the moving sample kit from falling forward or backward.

4. The combination according to claim 1, wherein the automatic fecal occult blood detector further comprises: a pressing member which is fixed on the transfer platform to press the excrement collector during the movement process of the sample kit.

5. The combination according to claim 4, wherein the pressing member is a pressure plate which comprises a lateral plate part fixed on the transfer platform and a plate hook part extending down from the top of the lateral plate part in a curved form, wherein the lower edge of the plate hook part forms a slope surface propped against the excrement collector.

6. The combination according to claim 4, wherein the pressing member is a rolling pressure member.

7. The combination according to claim 1, wherein the automatic fecal occult blood detector further comprises: a push plate mechanism which is provided on the discharging passage to push the sample kit out of the discharging passage and located at the downstream side of the image acquiring device along the conveyance direction of the discharging passage.

8. The combination according to claim 1, wherein the automatic fecal occult blood detector further comprises: a code scanner configured to acquire information of an identification tag adhered on the side of the transparent sleeve opposite to the test strip.

9. The combination according to claim 8, wherein the automatic fecal occult blood detector further comprises: a processing unit which is in signal connection with the code scanner and the image capturing device to process the image information captured by the image capturing device and the information read by the code scanner to generate a detection result.

10. The combination according to claim 1, wherein the automatic fecal occult blood detector further comprises: a gate provided on the feed passage to stop the sample kit.

* * * * *